(12) United States Patent
Nicolas et al.

(10) Patent No.: US 11,819,657 B2
(45) Date of Patent: Nov. 21, 2023

(54) PACKAGING DEVICE CONFIGURED TO CONTAIN AND DISPENSE A PLURALITY OF MEDICAL CONTAINERS

(71) Applicant: Becton Dickinson France, Le Pont de Claix (FR)

(72) Inventors: Maxime Nicolas, Grenoble (FR); Julien Gagliano, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 75 days.

(21) Appl. No.: 16/972,687

(22) PCT Filed: Jun. 12, 2019

(86) PCT No.: PCT/EP2019/065338
§ 371 (c)(1),
(2) Date: Dec. 7, 2020

(87) PCT Pub. No.: WO2019/238748
PCT Pub. Date: Dec. 19, 2019

(65) Prior Publication Data
US 2021/0252209 A1  Aug. 19, 2021

(30) Foreign Application Priority Data
Jun. 13, 2018  (EP) ..................... 18305725

(51) Int. Cl.
*A61M 5/00* (2006.01)
*A61M 5/32* (2006.01)
(52) U.S. Cl.
CPC .......... *A61M 5/002* (2013.01); *A61M 5/3205* (2013.01)

(58) Field of Classification Search
CPC ................ A61M 5/002; A61M 5/3205; A61B 2050/006; A61B 2050/0056;
(Continued)

(56) References Cited

U.S. PATENT DOCUMENTS 4,809,850 A * 3/1989 Laible .................. A61B 50/362
220/908
5,240,108 A * 8/1993 Tonna .................. A61B 50/362
211/84

(Continued)

FOREIGN PATENT DOCUMENTS

CN 102223851 A 10/2011
CN 102223852 A 10/2011
(Continued)

*Primary Examiner* — Steven A. Reynolds
(74) *Attorney, Agent, or Firm* — The Webb Law Firm (57) ABSTRACT

This packaging device includes a housing delimiting a storing chamber. The storing chamber includes a distribution aperture configured to allow passage of one of said medical containers outside the housing so as to allow a user to pick up this medical container. The packaging device also includes a sharps container positioned inside the storing chamber of the housing in a pre-use position, the sharps container being removable from the storing chamber so as to be put outside the housing in a collecting position wherein the sharps container allows collection of the used medical containers. The sharps container is configured to contain the plurality of medical containers in the pre-use position and comprises a spill-out window configured to allow the medical containers to fall down into the storing chamber when the sharps container is moved from the pre-use position to the collecting position.

14 Claims, 5 Drawing Sheets

(58) Field of Classification Search
CPC ........ A61B 2050/3013; A61B 50/3001; A61B 50/362; A61B 50/36; B65F 1/1607
USPC .................................... 206/366, 365, 438
See application file for complete search history.

(56) References Cited

U.S. PATENT DOCUMENTS

| | | | |
|---|---|---|---|
| 5,245,117 A | 9/1993 | Withers et al. | |
| 7,516,844 B2* | 4/2009 | Erickson | A61M 5/3205 206/365 |
| 7,694,811 B2* | 4/2010 | Brown | B65D 5/722 312/211 |
| 7,694,822 B2* | 4/2010 | Sullivan | A61B 17/3217 206/571 |
| 8,434,616 B2 | 5/2013 | Erickson et al. | |
| 8,875,881 B2* | 11/2014 | Smudde | A61B 50/362 206/366 |
| 8,915,362 B2 | 12/2014 | Erickson et al. | |
| 9,828,168 B2 | 11/2017 | Schmidt-Ellinger et al. | |
| 2003/0132129 A1* | 7/2003 | Erickson | A61M 5/3205 206/366 |
| 2003/0226879 A1* | 12/2003 | Auclair | B65D 5/721 229/122 |
| 2004/0099719 A1* | 5/2004 | Shadrach, III | B65D 5/18 229/122.1 |
| 2005/0269227 A1* | 12/2005 | Erickson | A61M 5/3205 206/362 |
| 2009/0114667 A1 | 5/2009 | Sansoucy et al. | |
| 2010/0084406 A1* | 4/2010 | Erickson | A61B 50/362 220/557 |

FOREIGN PATENT DOCUMENTS

| | | |
|---|---|---|
| CN | 105270676 A | 1/2016 |
| EP | 2057959 A2 | 5/2009 |
| WO | 2006119045 A1 | 11/2006 |
| WO | 2006119247 A1 | 11/2006 |

* cited by examiner

PACKAGING DEVICE CONFIGURED TO CONTAIN AND DISPENSE A PLURALITY OF MEDICAL CONTAINERS

CROSS-REFERENCE TO RELATED APPLICATIONS

This application is the United States national phase of International Application No. PCT/EP2019/065338 filed Jun. 12, 2019, and claims priority to European Patent Application No. 18305725.6 filed Jun. 13, 2018, the disclosures of which are hereby incorporated by reference in their entirety.

BACKGROUND OF THE INVENTION

The present invention relates to a packaging device configured to store and deliver a plurality of medical containers.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container contained in the packaging device of the invention, and the "proximal direction" is to be understood as meaning the opposite direction to said direction of injection, that is to say the direction towards the user's hand holding a medical container as for an injection operation.

Medical containers, such as prefilled syringes, may be filled with a pharmaceutical composition agent, such as a vaccine. These medical containers may then be distributed to health workers, for example nurses or pharmacists. Each medical container is usually contained in a blister pack configured to maintain the medical container in a sterile condition, this blister pack being put inside a box-shaped packaging device which enables to protect, store and transport the medical container. This packaging device is often configured to contain a single medical container. These individual packaging device however appear to be quite cumbersome when hundreds of medical containers are to be stored together and for instance be kept together at a low temperature in a fridge. There is therefore a need for a more compact packaging solution.

An aspect of the invention is a packaging device configured to contain a plurality of medical containers, the packaging device comprising:
  a housing delimiting a storing chamber, said storing chamber comprising a distribution aperture configured to allow passage of one of said medical containers outside the housing so as to allow a user to pick up said medical container;
  a sharps container positioned inside the storing chamber of the housing in a pre-use position, said sharps container being removable from the storing chamber so as to be put outside said housing in a collecting position wherein the sharps container allows collection of the used medical containers;
  the sharps container being configured to contain the plurality of medical containers in the pre-use position and the sharps container comprising a spill-out window configured to allow the medical containers to fall down from the sharps container into the storing chamber when the sharps container is moved from the pre-use position to the collecting position.

The packaging device according to the invention therefore allows to store a plurality of medical containers and to distribute these medical containers one-by-one. For a given number of medical containers, this multi-packaging device provides a less cumbersome packaging solution than individual packaging devices. Besides, the sharps container is contained in the housing. This improves compactness during transportation and storage.

More precisely, in pre-use position, the medical containers are contained within the sharps container, the sharps container being contained within the housing. The sharps container is configured so that, as long as it is contained within the housing, the medical containers are enclosed within the sharps container and cannot leave the sharps container and then the housing.

Before using the first medical containers, the user pulls out the sharps container from the housing. The sharps container is configured so that, when it is removed from the pre-use position, it releases the medical containers. The medical containers are discharged from the sharps container into the housing. The housing is thus configured to be used as a distributor of medical containers. As a matter of fact, once the medical containers are within the housing, they can go out through the distribution aperture. Once they have been used, the medical containers may be inserted again in the sharps container, placed outside from the housing. Once every medical container has been used and thrown into the sharps container, the sharps container may be either disposed or placed again in the housing.

By sharps container it should be understood a container that is configured to safely dispose sharp medical instruments after their use, such as syringes provided with contaminated needles. The sharps container is preferably rigid and may be made of a plastic material.

In an embodiment, the storing chamber of the housing comprises a guiding slope configured to guide the medical containers towards the distribution aperture.

In an embodiment, the sharps container comprises a guiding slope configured to guide the medical containers towards the spill-out window.

In an embodiment, the sharps container and the storing chamber have a complementary shape. More precisely, the sharps container is preferably configured to fit closely with the storing chamber. Two adjacent walls of the sharps container form an angle equal to the angle formed by two adjacent walls of the storing chamber.

In an embodiment, the sharps container comprises a shutter configured to close the spill-out window in a closing position and to allow passage of the medical containers through said spill-out window in an opening position.

In an embodiment, in the pre-use position, the shutter leans against the guiding slope of the storing chamber. This allows maintaining said shutter in its closing position while keeping the shutter ready to open. As the sharps container is being pulled out of the storing chamber, the shutter opens due to gravity and to the weight of the medical containers contained inside the sharps container.

In an embodiment, the shutter is rotatably mounted on a wall of the sharps container. This prevents the medical containers from falling too quickly. As a result, this prevents the medical containers from being askew and obstructing movement of the medical containers towards the distribution aperture.

In an embodiment, the sharps container comprises securing means configured to secure the shutter in the closing position, said securing means being configured to be inactivated in the pre-use position of the sharps container. This permits the shutter to open because of gravity and the weight of the medical containers when the sharps container is being removed, while allowing sealing the sharps container once the contaminated medical containers have been gathered into the sharps container.

In an embodiment, the sharps container comprises a grasping member configured to allow a user to pull out the sharps container from the storing chamber.

Advantageously, the housing comprises a drawer that can be opened to define the distribution aperture.

In an embodiment, the housing comprises an abutment member protruding from the distribution aperture to prevent the medical containers from falling down through said distribution aperture. The abutment members permit to maintain at least one of these medical containers accessible to a user.

In an embodiment, the housing comprises data retrieve means configured to retrieve data contained in each medical container when said medical container exits the housing through the distribution aperture. This allows collecting useful information such as the number of medical containers remaining inside the packaging device, tracking the medical containers, logging a date or use hour of each medical container, etc.

In an embodiment, the distribution aperture is dimensioned to allow the passage of a single medical container at once.

In an embodiment, the housing comprises refrigeration means configured to refrigerate the medical containers contained inside the housing. This allows storing the packaging device outside a fridge, without damaging the pharmaceutical composition agent contained in the medical containers.

In an embodiment, the storing chamber is a first storing chamber and the housing comprises a second storing chamber separated from the first storing chamber by said guiding slope, said second storing chamber having a distribution aperture allowing passage of one medical container of a second plurality of medical containers, and wherein the packaging device further comprises a second removable sharps container configured to contain said second plurality of medical containers and comprising a spill-out window that permits the second plurality of medical containers to fall down into the second storing chamber when the second sharps container is removed from the housing.

In an embodiment, the packaging device comprises the medical containers, each medical container comprising a cylindrical protection tube. The protection tube protects the syringe when the medical containers spill out into the storing chamber. The cylindrical shape permits the medical containers to roll efficiently onto the guiding slope towards the distribution aperture.

The syringe is preferably a prefilled syringe.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1:
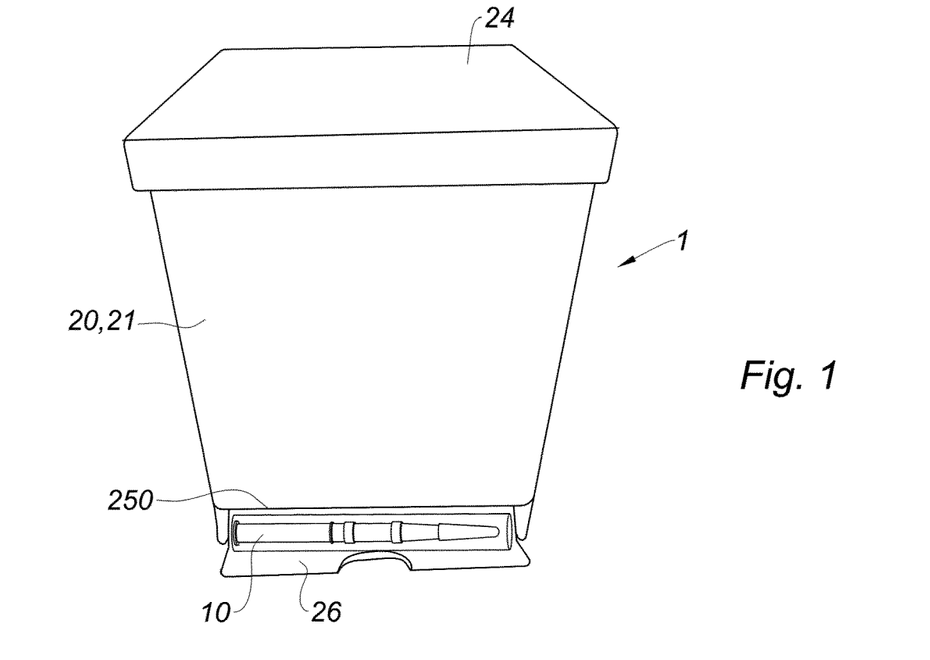
FIG. 1 is a perspective view of a packaging device according to an embodiment of the invention.
Figure 5:
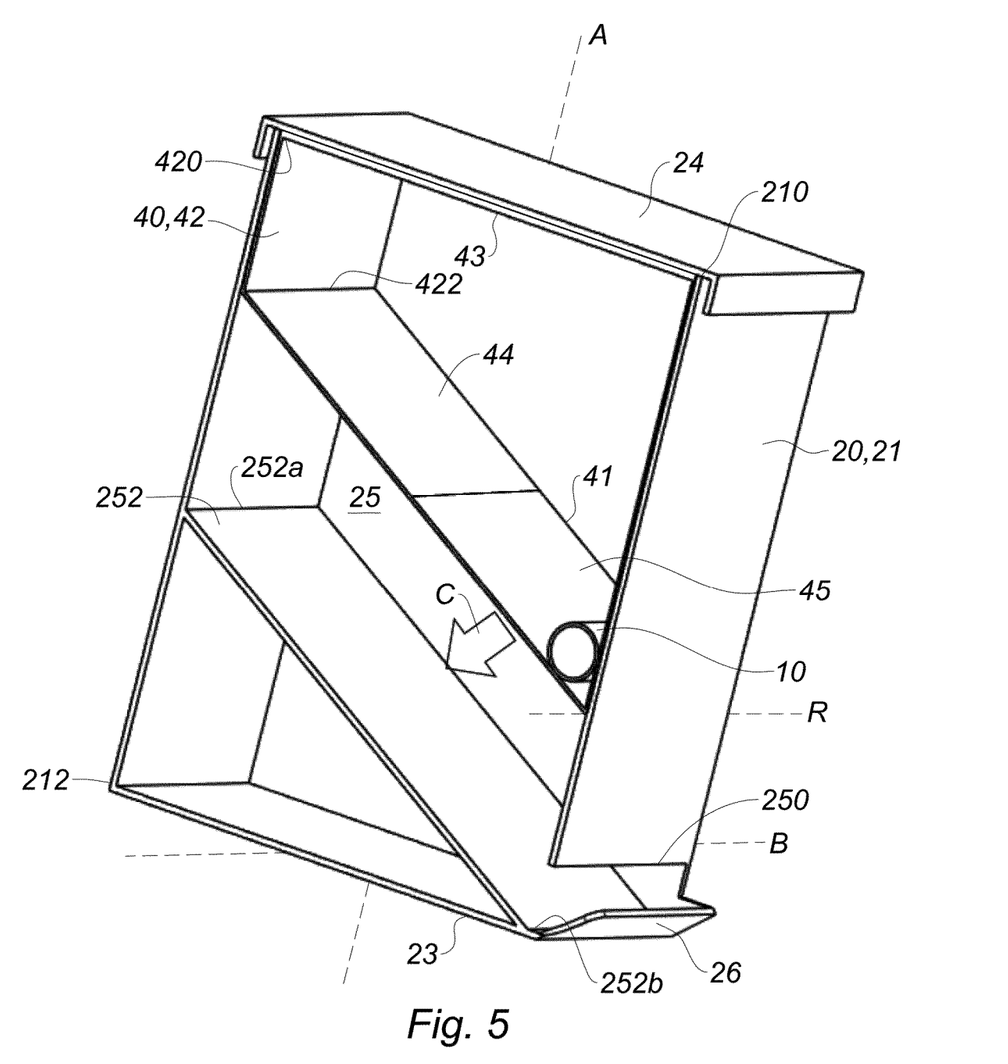
FIG. 5 is a cross-section view of a packaging device according to an embodiment of the invention.

With reference to FIGS. 1 and 5 is shown a packaging device 1 according to an embodiment of the invention. The packaging device 1 is configured to contain and distribute a plurality of medical containers 10, such as for example a hundred or more of medical containers 10. The medical containers 10 may be prefilled syringes. The syringes may be prefilled with a pharmaceutical composition agent, such as a vaccine, a medicine or a therapeutic agent. For instance, the medical containers 10 may be flu-vaccine prefilled syringes.

The packaging device 1 comprises a box-shaped housing 20 configured to allow storing and distribution of the medical containers 10, preferably one-by-one, and a removable sharps container 40, configured to collect the medical containers 10 after use.

Figure 9:
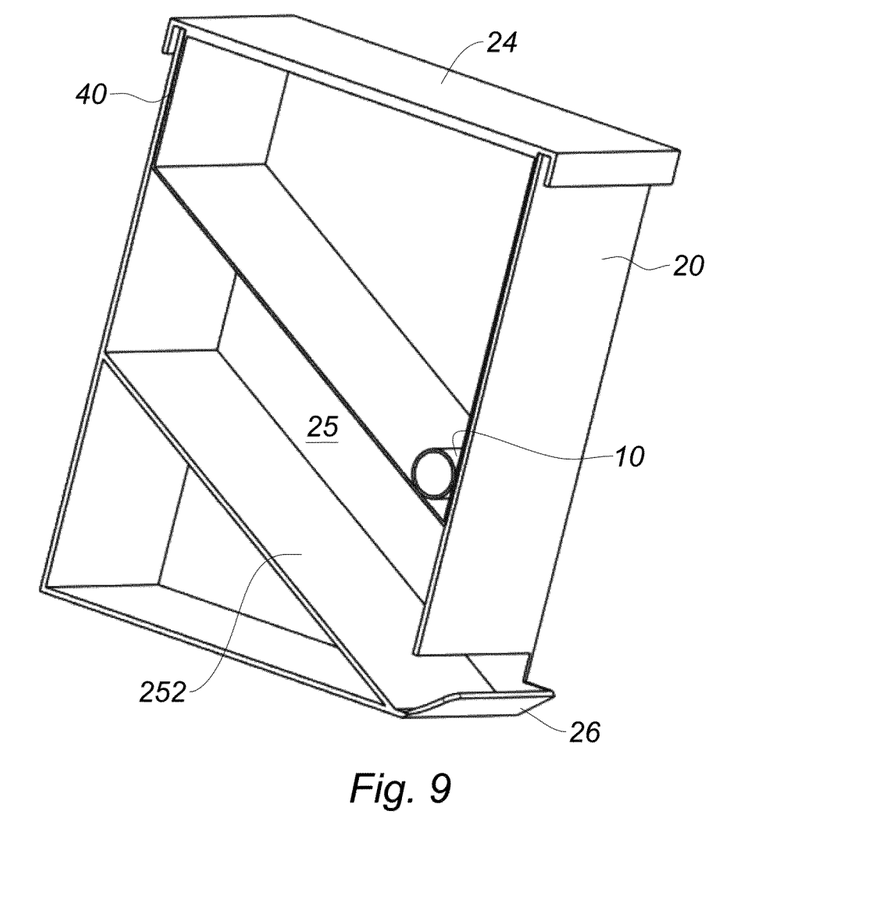
FIG. 9 is a perspective view of a packaging device according to an embodiment of the invention.

The sharps container 40 is movable relative to the housing 20 between:
- a pre-use position (FIGS. 1, 2, 5) wherein the sharps container 40 is inside the housing 20. The sharps container 40 is configured to contain the medical containers 10 before use,
- a collecting position (FIGS. 3, 4) wherein the sharps container 40 is outside the housing 20 in order to collect the used medical containers 10, and
- a post-use position (FIG. 9) wherein the sharps container 40 is inside the housing 20 in order to contain the used medical containers 10. The pre-use position and the post-use position may be similar.

The box-shaped housing 20 may have a lateral wall 21 extending around a longitudinal axis A. The lateral wall 21 may have four faces preferably parallel to the longitudinal axis A. Adjacent faces may be orthogonal. The box-shaped housing may be a rectangular cuboid. In an embodiment, the housing 20 has a cubic shape. The housing 20 may be made of cardboard or plastic.

The housing 20 has an access opening 22 configured to allow removal or insertion of the sharps container 40 from or inside the housing 20. The access opening 22 may be delimited at a first end 210 of the lateral wall 21. A second end 212, opposite the first end 210, may be provided with a bottom wall 23 that permits the housing 20 to rest on a flat surface.

The housing 20 may also include a lid 24 configured to close the access opening 22. The lid 24 may be removable from the housing or may be rotatably mounted on the lateral wall 21, for example on the first end 210. The housing 20 may comprise securing means, such as snap-fit elements, configured to maintain the lid 24 in a closed position.

Figure 6:
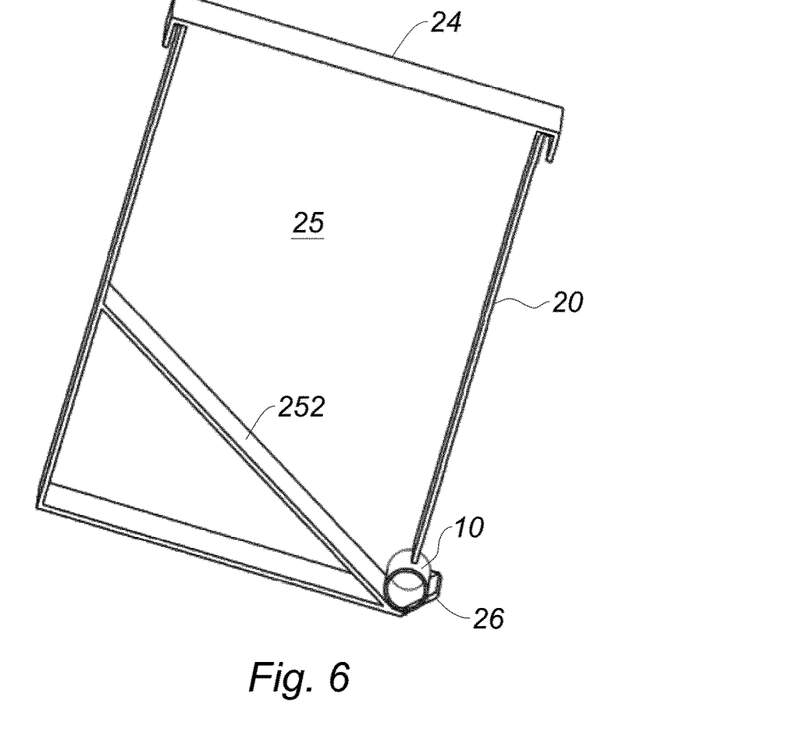
FIGS. 6 and 7 are cross-section views of a packaging device according to an embodiment of the invention.
Figure 7:
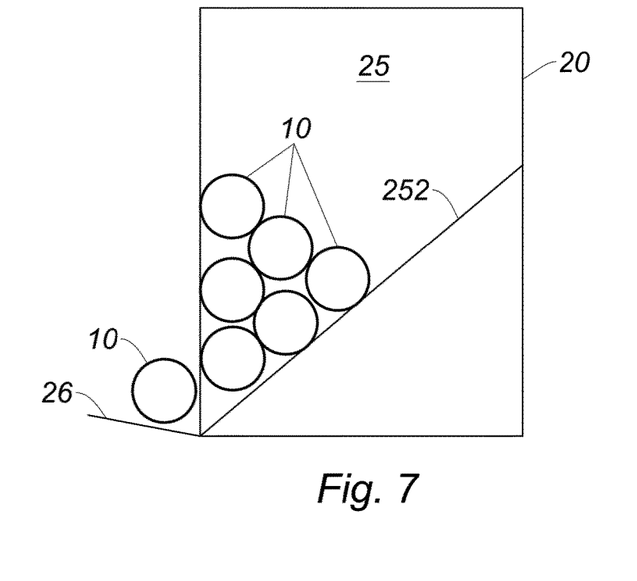

The housing 20 comprises a storing chamber 25 configured to contain the sharps container 40 when the sharps container 40 is in the pre-use or post-use position, and to contain the plurality of medical containers 10 when the sharps container 40 is in the collecting position as shown on FIGS. 6 and 7. Preferably, the sharps container 40 and the storing chamber 25 have a complementary shape so that the packaging device 1 can store a high number of medical containers 10.

With reference to FIG. 5, the storing chamber 25 comprises a distribution aperture 250 configured to allow passage of the medical containers 10 outside the housing 20 so as to allow a user to pick up said medical container 10. The distribution aperture 250 is preferably designed to allow the passage of a single medical container at once, so that the medical containers 10 are dispensed one-by-one. The distribution aperture 250 may have a rectangular shape. The distribution aperture 250 may be defined by a drawer that can be pulled out in order to open the distribution aperture 250.

As shown on the figures, the distribution aperture 250 may be provided through the lateral wall 21, for example at the second end 212 of said lateral wall 21. Preferably, the distribution aperture 250 is provided through a single face of the lateral wall 21.

The storing chamber 25 may also include a guiding slope 252 extending inside the housing 20 and configured to let the medical containers 10 move by gravity towards the distribution aperture 250 after the sharps container 40 is removed. The guiding slope 252 may define a planar guiding surface. As visible on the Figures, the guiding slope 252 forms an acute angle with a horizontal plane orthogonal to the longitudinal axis A.

The guiding slope 252 may have a top end 252a at an intermediate portion of one face of the lateral wall 21, and a bottom end 252b at the second end 212 of an opposite face the lateral wall 21. In an embodiment not shown, the guiding slope 252 may have a top end 252a at the first end 210 of one face of the lateral wall 21, while the bottom end 252b is at the second end 212 of an opposite face the lateral wall 21, so that the guiding slope 252 diagonally extends inside the housing 20. The distribution aperture 250 may be adjacent to the bottom end 252b of the guiding slope 252.

The guiding slope 252, the lateral wall 21 and the lid 24 delimit the storing chamber 25.

The housing 20 advantageously comprises an abutment member 26 configured to stop the fall of the medical containers 10 rolling on the guiding slope 252. The abutment member 26 enables to maintain at least one medical container 10 accessible to a user. The abutment member 26 may be located at an edge of the distribution aperture 250, and may protrude from the lateral wall 21, more precisely from the second end 212 of the lateral wall 21.

The abutment member 26 may be an abutment wall, as illustrated on the Figures, which forms an angle with the guiding slope 252. The abutment member 26 may be fixed relative to the housing 20, or may be movable between a closing position wherein the abutment member 26 closes the distribution aperture 250 and an opening position wherein the abutment member 26 allows medical containers 10 to pass though the distribution aperture 250. The housing 20 may comprises securing means, such as snap-fit elements, in order to maintain the abutment member 26 in the closing position. The abutment member 26 may advantageously comprise two sidewalls preventing a lateral fall of the medical containers 10.

Figure 8:
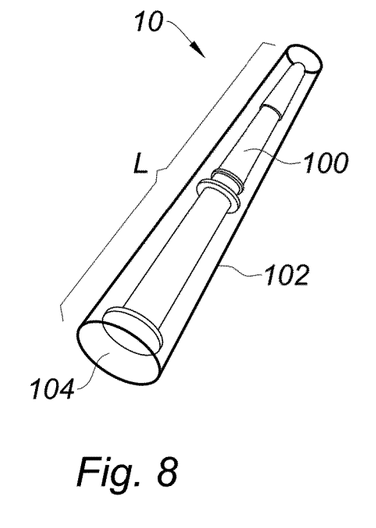
FIG. 8 is a perspective view of a medical container intended to be stored and distributed by the packaging device of the invention

As can be seen on FIG. 8, the medical containers 10 may include a syringe 100, such as a prefilled syringe, and a protection tube 102 containing this syringe 100. The protection tube 102 preferably has a cylindrical shape so as to roll on the guiding slope 252. The protection tube 102 may be transparent. In the illustrated embodiment, the protection tube 102 comprised an open end which is sealed by a sealing element 104. The protection tube 102 and the sealing element 104 are configured to maintain the syringe 100 in a sterile atmosphere. The sealing element 104, such as an aluminum sheet, may be peeled off by a user before use of the syringe 100.

The medical containers 10 are arranged parallel to each other inside the sharps container 40 in the pre-use position and inside the distribution chamber 25 when the sharps container 40 is in the collecting position.

Preferably, the medical containers 10 longitudinally extend inside the packaging device along a transverse direction B which may be orthogonal to the longitudinal axis A, and preferably parallel to a longitudinal direction of the distribution aperture 250.

In the pre-use position, a first half of the medical containers 10 may have its distal end pointing at a first direction along axis B, while a second half of the medical containers 10 may have its distal end pointing at an opposite second direction along axis B. This permits to balance the weight of the plurality of medical containers 10 inside the packaging device 1 before use.

In order to prevent some medical containers 10 from being askew inside the housing 20, and thus in order to avoid any blocking, the packaging device 1 may comprise maintaining means configured to maintain the medical containers 10 parallel to each other. For example, the maintaining means comprise a connecting belt (not shown) connecting the medical containers 10 to each other in the manner of a cartridge belt.

As visible on the Figures, a width of the storing chamber 25 may be comprised between 100% and 130%, preferably between 100% and 110% of the length of the medical containers 10, more precisely the length L of the protection tube 102. The width of the storing chamber 25 may be correspond to the distance along the transverse axis B between two opposite faces of the housing 20.

With reference to FIGS. 2 to 5, the sharps container 40 defines an internal volume configured to contain the plurality of medical containers 10 before their use. The sharps container 40 comprises a spill-out window 41 configured to permit the medical containers 10 to leave the sharps container 40 and spill out into the storing chamber 25 when the sharps container 40 is moved from the pre-use position to the collecting position.

The sharps container 40 may comprise a lateral wall 42 which may have four faces, the adjacent faces being for example orthogonal to each other. The sharps container 40 may further comprise a supporting wall 43, for example provided at a first end 420 of the lateral wall 42. The supporting wall 43 is advantageously configured to allow the sharps container 40 resting on a flat surface when the sharps container 40 is in the collecting position.

The sharps container 40 advantageously comprises a guiding slope 44 configured to guide the medical containers 10 towards the spill-out window 41 when the sharps container 40 is removed from the pre-use position. The guiding slope 44 defines a planar surface onto which the medical containers 10 can roll. The guiding slope 44 is inclined relative to the lateral wall 42 and may be provided at a second end 422 thereof, opposite said first end 420. It should be noted that the spill-out window 41 is located at the furthest end of the guiding slope 44 from the supporting wall 43.

The guiding slope 44 of the sharps container 40 and the guiding slope 252 of the storing chamber 25 are preferably parallel to each other. Although not shown on the figures, in the pre-use and post-use position, the guiding slope 44 of the sharps container 40 may lean against the guiding slope 252 of the housing 20 so that the sharps container 40 occupies the whole volume of the storing chamber 25.

With reference to FIG. 5, the sharps container 40 advantageously comprises a shutter 45 movable between a closing position (FIG. 5) wherein the shutter 45 closes the spill-out window 41 and a release position (not shown) wherein the shutter 45 allows passage of the medical containers 10 through the spill-out window 41. In the closing position, the shutter 45 may be coplanar with the guiding slope 44.

For example, the shutter 45 is rotatably mounted on the sharps container 40 so that the shutter 45 opens in direction of the top end 252*a* of the guiding slope 252. The rotation axis R of the shutter 45 may be parallel to the transverse axis B, more precisely to the distribution aperture 250. This rotation axis may be located at the furthest end of the shutter 45 from the supporting wall 43.

The lateral wall 42, the supporting wall 43, the guiding slope 44 and the shutter 45 delimit the internal volume of the sharps container 40.

In an embodiment not shown, the sharps container 40 comprises securing means configured to secure the shutter 45 in the closing position. These securing means may be configured to be inactive in the pre-use position and to be activated before the sharps container 40 is moved from the collecting position to the post-use position. The securing means may comprise snap-fit elements or an adhesive covered by a covering sheet that a user has to peel off so as to activate the securing means.

Preferably, in the pre-use position, the shutter 45 is not secured and leans against the guiding slope 252 of the storing chamber 25. This allows maintaining the shutter 45 in its closing position and allows the shutter 45 to open due to gravity as soon as the sharps container 40 is pulled out the housing 20.

Figure 2:
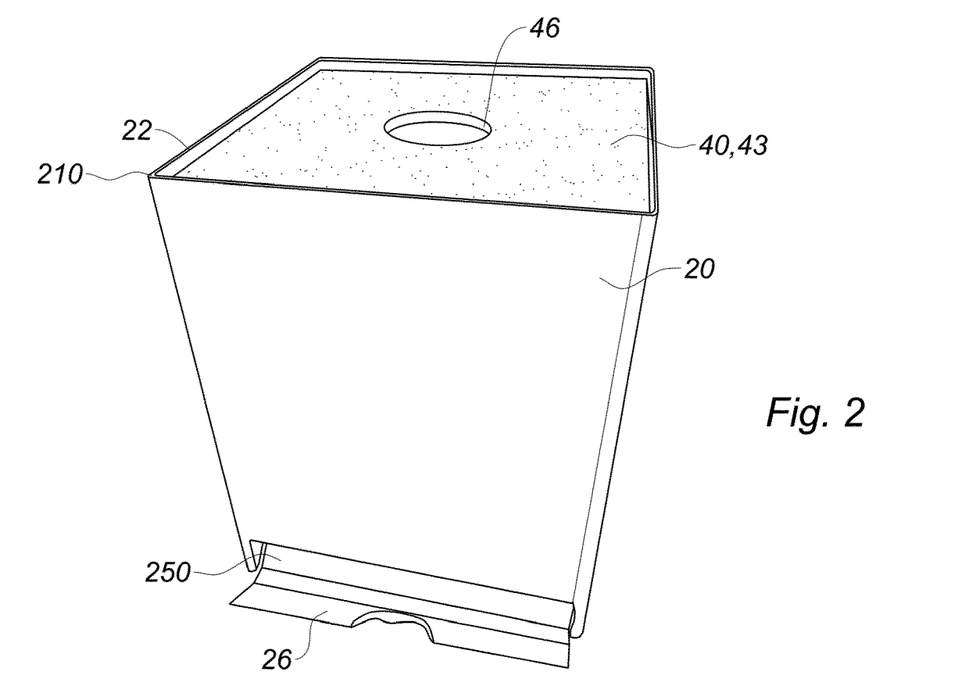
FIG. 2 is a perspective view of a packaging device according to an embodiment of the invention, the sharps container being in the pre-use position.

With reference to FIG. 2, the sharps container 40 advantageously comprises a grasping member 46 configured to allow a user to pull out the sharps container 40 easily from the storing chamber 25 of the housing 20. The grasping member 46 may be an opening into which the user may pass a finger. For example, the grasping member 46 is located on the supporting wall 43.

In an embodiment not shown, the packaging device 1, more precisely the housing 20 or the sharps container 40, may comprise data retrieving means configured to retrieve data contained in each medical container 10 for example when said medical container 10 exits the housing 20 through the distribution aperture 250 or when said medical container 10 after use is collected inside the sharps containers 40. For example, the medical containers 10 may each comprise a RFID tag and the housing 20, or the sharps container 40, may comprise a reader configured to read the RFID tags of the medical containers. One reader may be located in the abutment member 26. Another reader may be located in the shutter 45.

The data retrieving means may serve to count the number of used medical containers 10 in order to permit a user to know how many unused medical containers 10 there are left inside the storing chamber 25. Alternatively, the packaging device may comprise a visual indicator, such as a number marked on a connecting belt connecting all the medical containers 10.

It should also be noted that the packaging device 1 may, more precisely the housing 20, may advantageously comprise refrigeration means configured to refrigerate the medical containers 10, such as a coolant circuitry known for a skilled person. The refrigeration means may be active or passive.

In an embodiment not shown, the housing 20 delimits two storing chambers 25, which may be inverted relative to each other. Each storing chamber 25 comprises a distribution aperture 250. The packaging device 1 then comprises two sharps containers 40, each configured to be received inside a corresponding one of the two storing chambers 25 and each configured to receive a plurality of medical containers 10. The two storing chambers 25 may be separated by the guiding slope 252. This guiding slope 252 may be common to the two storing chambers 25. A first face of the guiding slope 252 is advantageously configured to guide a first plurality of medical containers 10 towards the distribution aperture 250 of a first one of the two storing chambers 25, while a second face of the guiding slope 252, opposite the first face, is configured to guide a second plurality of medical containers 10 towards the distribution aperture 250 of the second one of the two storing chambers 25. The guiding slope 252 advantageously extends diagonally inside the housing 20. For example, the top end 252*a* of the guiding slope 252 is located at the first end 210, and the bottom end 252*b* of the guiding slope 252 is located at the second 212. This packaging device having two storing chambers 25 and two sharps containers 40 may also comprise some or all of the above-described packaging device 1.

The operation of the packaging device 1 is described below.

With reference to FIG. 1, the packaging device 1 contains a plurality of medical containers 10, such as flu-vaccine prefilled syringes. The medical containers 10 are ready to be used. These medical containers 10 are stored in the sharps container 40, which is in the pre-use position, that is to say located inside the housing 20, more precisely inside the storing chamber 25. The packaging device 1 may be stored inside a fridge so as to store and keep the medical containers 10 at a predetermined temperature. When a user needs to use the medical containers 10, the user may take the packaging device 1 out of the fridge.

With reference to FIG. 2, the user has to withdraw the lid 24 so as to access the sharps container 40. Thanks to the grasping member 46, the user can pull the sharps container 40 out of the storing chamber 25. By doing so, the shutter 45, no more leans against the guiding slope 252. Due to gravity and the weight of the medical containers 10 above the shutter 45, this shutter 45 automatically opens (see arrow C on FIG. 5) and the medical containers 10 can flow outside the sharps container 40 through the spill-out window 41, guided by the guiding slope 44 towards said spill-out window 41. The medical containers 10 fall down against the guiding slope 252. Due to gravity and to their cylindrical shape, the medical containers 10 roll on the guiding slope 252 towards the distribution aperture 250, as shown on FIGS. 6 and 7.

Figure 3:
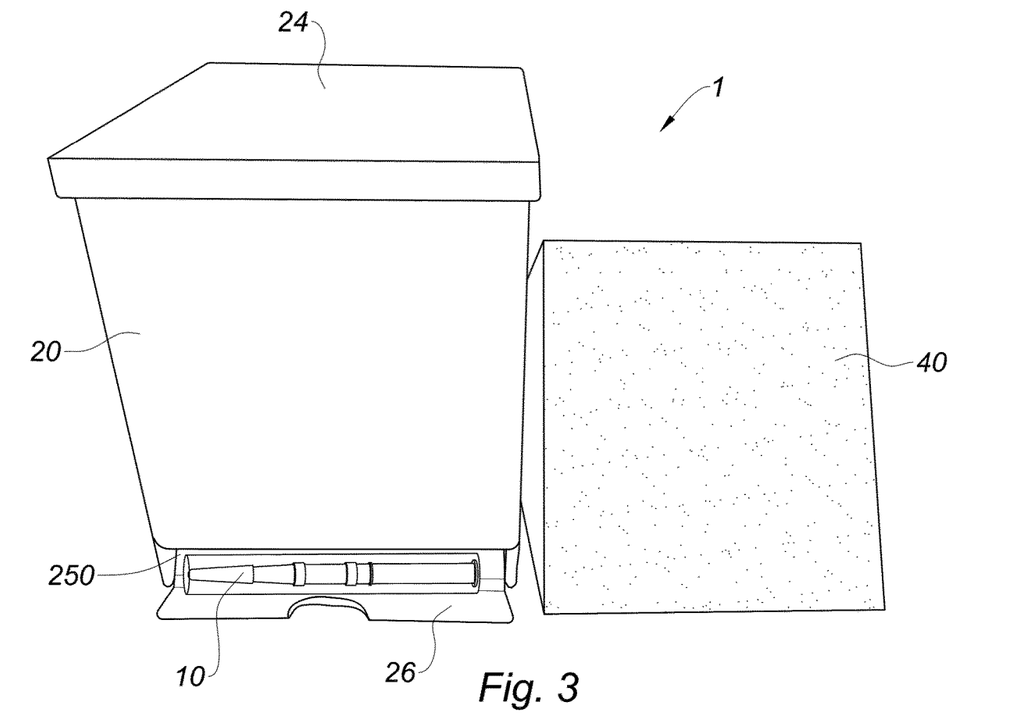
FIG. 3 is a perspective view of a packaging device according to an embodiment of the invention, the sharps container being in the collecting position.
Figure 4:
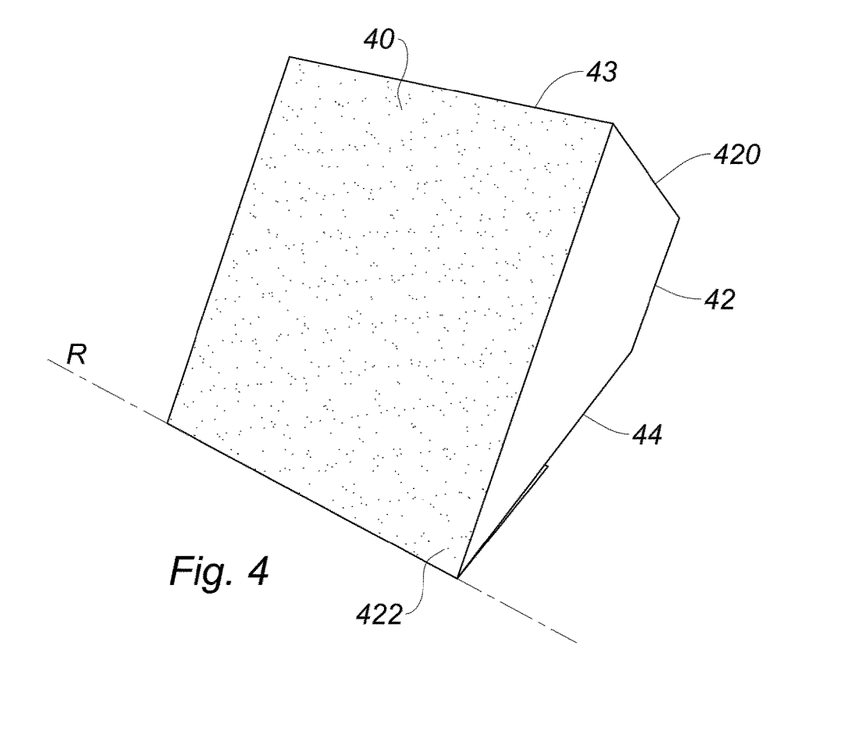
FIG. 4 is a perspective view of a sharps container of a packaging device according to an embodiment of the invention.

With reference to FIGS. 3 and 4, the user can place the sharps container 40 in the collecting position. In this collecting position, the supporting wall 43 preferably rests against a flat surface.

The user may then open the distribution aperture 250 by moving the abutment member 26 in the opening position, so that a first one of the medical containers 10 may pass through the distribution aperture 250 and become accessible to the user.

The user can grasp and use the accessible medical container 10. As soon as this medical container 10 is withdrawn from the distribution aperture 250, another medical container 10 of the plurality of medical containers automatically moves through the distribution aperture 250 until be stopped by the abutment member 26.

Once the medical container 10 is used, the user may put it inside the sharps container 40 which is in the collecting position. The user has to pass the used medical container 10 through the spill-out window 41, so that this contaminated medical container is safely collected inside the sharps container 40.

If the user has not used all the medical containers 10 and wants to keep them for a later use, then the user may put the housing 20 inside the fridge so as to maintain the medical containers 10 left at a predetermined temperature. The contaminated medical containers 10 remain inside the sharps container 40 which is kept outside the housing 20 and outside the fridge.

When the user is informed, for example by a visual indicator, that there are only a few medical containers 10 left inside the storing chamber 25, then the user may order another packaging device 1 containing another plurality of medical containers 10.

Once all the medical containers 10 have been used and collected inside the sharps container 40, and if the packaging device 1 has two storing chambers 25, the user may turn this packaging device 1 upside down so as to access the second lid 24, the second storing chamber 25 and the second sharps container 40. The user may then repeat the above-described operations.

Once all the medical containers 10 initially contained in the packaging device 1 are used and now collected inside the single or the two sharps container 40, the user may then close the spill-out window 41 of each sharps container 40 by activating the securing means and moving the shutter 45 towards the closing position. The user may then move the sharps container 40 in the post-use position, that is to say replace the sharps container 40 inside the corresponding storing chamber 25. The user may then close the lid 24 and send the packaging device 1 back for example recycling operation.

The invention claimed is:

1. A packaging device configured to contain a plurality of medical containers, the packaging device comprising:
    a housing delimiting a storing chamber, said storing chamber comprising a distribution aperture configured to allow passage of one of said medical containers outside the housing so as to allow a user to pick up said medical container; and
    a sharps container positioned inside the storing chamber of the housing in a pre-use position, said sharps container being removable from the storing chamber so as to be put outside said housing in a collecting position wherein the sharps container allows collection of used medical containers,
    wherein the sharps container is configured to contain the plurality of medical containers in the pre-use position and the sharps container comprises a spill-out window configured to allow the medical containers to fall down from the sharps container into the storing chamber when the sharps container is moved from the pre-use position to the collecting position, and
    wherein the sharps container comprises a shutter configured to close the spill-out window in a closing position when the sharps container is in the pre-use position and to allow passage of the medical containers into the storing chamber and through said spill-out window in an opening position when the sharps container is moved from the pre-use position to the collecting position.

2. A packaging device configured to contain a plurality of medical containers, the packaging device comprising:
    a housing delimiting a storing chamber, said storing chamber comprising a distribution aperture configured to allow passage of one of said medical containers outside the housing so as to allow a user to pick up said medical container; and
    a sharps container positioned inside the storing chamber of the housing in a pre-use position, said sharps container being removable from the storing chamber so as to be put outside said housing in a collecting position wherein the sharps container allows collection of used medical containers,
    wherein the sharps container is configured to contain the plurality of medical containers in the pre-use position and the sharps container comprises a spill-out window configured to allow the medical containers to fall down from the sharps container into the storing chamber when the sharps container is moved from the pre-use position to the collecting position, and
    wherein the sharps container comprises a shutter configured to close the spill-out window in a closing position and to allow passage of the medical containers into the storing chamber and through said spill-out window in an opening position, wherein the storing chamber of the housing comprises a guiding slope configured to guide the medical containers towards the distribution aperture, and wherein the guiding slope extends inside the housing from an intermediate portion of a first lateral wall of the housing and a bottom end of a second lateral wall, the second lateral wall opposite the first lateral wall.

3. The packaging device according to claim 1, wherein the sharps container comprises a guiding slope configured to guide the medical containers towards the spill-out window.

4. The packaging device according to claim 1, wherein the sharps container and the storing chamber have a complementary shape.

5. The packaging device according to claim 1, wherein in the pre-use position, the shutter leans against a guiding slope of the storing chamber.

6. The packaging device according to claim 1, wherein the shutter is rotatably mounted on a wall of the sharps container.

7. The packaging device according to claim 1, wherein the sharps container comprises securing means configured to secure the shutter in the closing position, said securing means being configured to be inactivated in the pre-use position of the sharps container.

8. The packaging device according to claim 1, wherein the sharps container comprises a grasping member configured to allow a user to pull out the sharps container from the storing chamber.

9. The packaging device according to claim 1, wherein the housing comprises an abutment member protruding from the distribution aperture to prevent the medical containers from falling down through said distribution aperture.

10. The packaging device according to claim 1, wherein the housing comprises data retrieve means configured to retrieve data contained in each medical container when said medical container exits the housing through the distribution aperture.

11. The packaging device according to claim 1, wherein the distribution aperture is dimensioned to allow passage of a single medical container at once.

12. The packaging device according to claim 1, wherein the housing comprises refrigeration means configured to refrigerate the medical containers contained inside the housing.

13. The packaging device according to claim 2, wherein the storing chamber is a first storing chamber and the housing comprises a second storing chamber separated from the first storing chamber by said guiding slope, said second storing chamber having a second distribution aperture allowing passage of one medical container of a second plurality of medical containers, and wherein the packaging device further comprises a second removable sharps container configured to contain said second plurality of medical containers and comprising a spill-out window that permits the second plurality of medical containers to fall down into the second storing chamber when the second sharps container is removed from the housing.

14. The packaging device according to claim 1, wherein the packaging device comprises the medical containers, each medical container comprising a cylindrical protection tube.

* * * * *